United States Patent [19]
Rup et al.

[11] Patent Number: 4,940,782
[45] Date of Patent: Jul. 10, 1990

[54] MONOCLONAL ANTIBODIES AGAINST IGE-ASSOCIATED DETERMINANTS, HYBRID CELL LINES PRODUCING THESE ANTIBODIES, AND USE THEREFORE

[75] Inventors: Bonita J. Rup; Larry E. Kahn, both of St. Louis, Mo.

[73] Assignee: G. D. Searle & Co., Chicago, Ill.

[21] Appl. No.: 59,749

[22] Filed: Jun. 8, 1987

[51] Int. Cl.$^5$ .................. C12N 5/20; C07K 15/28; A61K 39/00

[52] U.S. Cl. .................. 530/387; 435/240.27; 435/948; 435/70.21; 436/513; 424/85.8; 530/809; 935/104; 935/107

[58] Field of Search .................. 435/240.27, 68, 172.2, 435/948; 530/387, 388, 809; 424/85.8; 436/513, 548; 935/100, 104, 107, 108, 110

[56] References Cited

PUBLICATIONS

Conrad, D. H. et al., "Properties of Two Monoclonal Antibodies Directed Against the Fc and Fab' Regions of Rat IgE," *Int. Arch. Allergy Appl. Immunol.* 70:352–360, 1983.

Stanworth, D. R. et al., "Anti-E-Chain Antibodies as Probes in the Study of Mast-Cell Triggering," *Molec Immunol.* 23(11): 1231–1235, 1986.

*Mouse Monoclonal Antibody to Rat Epsilon Heavy Chain*, Serotec, Code No.: MCA 193.

*Primary Examiner*—Margaret Moskowitz
*Assistant Examiner*—Kay E. Cheney
*Attorney, Agent, or Firm*—Paul D. Matukaitis; Mary Jo Kanady

[57] ABSTRACT

The present invention is directed to monoclonal antibodies and hybridomas which produce them, which react with IgE when it is unbound and thereby inhibit IgE binding to mast cells, and react with IgE when it is bound to the B-cell FcE receptor, but do not react with IgE when it is bound to the mast cell FcE receptor.

2 Claims, 5 Drawing Sheets

MAB-44.7B DOES RECOGNIZE IgE BOUND TO A
B-LYMPHOCYTE LOW AFFINITY FcE RECEPTOR

FIG.5

MONOCLONAL ANTIBODIES AGAINST IGE-ASSOCIATED DETERMINANTS, HYBRID CELL LINES PRODUCING THESE ANTIBODIES, AND USE THEREFORE

FIELD OF THE INVENTION

This invention is directed to monoclonal antibodies against determinants present on IgE, hybrid cell lines producing these antibodies, and methods of using these monoclonal antibodies.

BACKGROUND OF THE INVENTION

An immediate hypersensitivity response of the immune system can occur through the interaction of immunoglobulin E (IgE) and the receptor for IgE (FcE) present on the surface of mast cells and basophils in the presence of antigen which is capable of reacting with the FcE bound IgE.

The mast cell FcE receptors have a high affinity for the Fc region of the IgE molecule. Thus, when IgE becomes bound to the FcE receptor the specific antigen binding domains of the IgE molecule face outward from the mast cell to enable antigen specific binding to occur.

A key event in the initiation of allergic reactions is the high affinity binding of IgE to FcE receptors on mast cells or basophils (Ishizaka, et al., *Journal of Immunology*, 99: 1187, 1967). Subsequent cross-linking of mast cell bound IgE bound to adjacent FcE receptors activates the mast cell and results in degranulation. In so doing, the mast cells release a variety of the mediators such as histamine, serotonin and slow-reacting substance which cause many of the symptoms associated with allergies.

Cross-linking of the mast cell IgE receptor (FcE) and the resultant triggering of the mast cell can occur indirectly, when IgE is bound to nearby FcE receptors, or directly, using antibody specific for the FcE receptors themselves. Indirect cross-linking can occur when specific antigen is bound by IgE molecules on the cell surface, or by using anti-idiotype antibody, lectins, or anti-IgE molecule antibodies reactive with epitopes which are accessible even when the IgE is bound by the FcE receptor.

In addition to the high affinity FcE receptors on mast cells and basophils, receptors with low affinity for IgE have been detected on a number of other cell types including B and T lymphocytes, monocytes, eosinophils and platelets (Lawrence, et al., *Journal of Clinical Investigation*, 55: 268, 1975). There is little or no structural similarity between the high and low affinity FcE receptors. Recently, the alpha chain of the high affinity mast cell receptor (Kinet, et al., *Federation Proceedings (Abstract 6006)*, 46: 1346, 1987) and the low affinity receptor from B lymphocytes (Kikutani, et al., *Cell*, 47: 657, 1986) have been cloned. No sequence homology was detectable between the two receptors. Furthermore, there is evidence that even low affinity receptors expressed on different hematopoietic cells are heterogeneous since a monoclonal antibody to the murine B lymphocyte FcE receptor failed to react with mouse T cells or macrophages (Rao, et al. *Journal of Immunology*, 138: 1845, 1987).

The function of FcE receptors on different cell lineages is likely to be different. While FcE receptors on eosinophils and macrophages are probably involved in antibody-dependent cytotoxicity, receptors for IgE on lymphocytes are probably involved in immune regulation (Metzger, et al., *Annual Reviews of Immunology*, 4: 419, 1986).

SUMMARY OF THE INVENTION

It is an object of the present invention to provide a monoclonal antibody that is capable of binding to IgE when it is unbound and will not block binding of IgE to the B-cell low-affinity FcE receptor, but will inhibit binding of IgE to the mast cell high-affinity FcE receptor.

It is another object of the present invention to provide methods for ameliorating the immediate hypersensitivity response.

Thus, the present invention relates to monoclonal antibodies reactive with free IgE and with IgE bound to FcE receptors on B-cells, but which are non-reactive with IgE bound to FcE receptors on mast cells. The invention further includes hybrid cell lines which produce these antibodies as well as methods of using and processes of preparing these monoclonal antibodies.

Present monoclonal antibodies of possible use in ameliorating the immediate hypersensitivity response have certain drawbacks with respect to their specificity. Regrettably, the existence of monoclonal antibodies which are capable of preventing the binding of IgE to the FcE receptor present on mast cells while allowing the binding of IgE to the FcE receptor present on B-cells have not been demonstrated. A need exists for monoclonal antibodies that will prevent the immediate hypersensitivity reaction by blocking the binding of IgE to FcE receptors on mast cells, but do not interfere with the binding of IgE to B-cell FcE receptors.

The ability to preferentially react with IgE and thereby prevent the binding of IgE to the mast cell FcE receptor, while at the same time not suppressing the ability of IgE to bind to the B-cell FcE receptor, is very significant. By having such selective reactivity the monoclonal antibodies of the invention are capable of suppressing the immediate hypersensitivity responses associated with the binding of IgE to the mast cell FcE receptor, but do not interfere with the normal immune regulatory events associated with the ability of IgE to bind to the B-cell FcE receptor. Since these monoclonal antibodies do not react with IgE when it is bound to the mast cell FcE receptor, these monoclonal antibodies cannot cause mast cell FcE receptor cross-linking and thereby cause the mast cell triggering resulting in degranulation when the monoclonal antibodies of the invention are used immunotherapeutically. However, since the antibodies do not interfere with the binding of IgE to the B-cell FcE receptor, the immune regulatory effects, or any B-cell activation potential, of such interaction are not significantly hindered.

In addition, since the monoclonal antibodies of the invention bind to an epitope on IgE within or near the IgE Fc domain which interacts with the mast cell FcE receptor, the antibodies can be used to map the receptor interaction sites. This information, in turn, is useful in designing peptides or other agents which will mimic the antibody in inhibiting the binding of IgE to mast cells.

DETAILED DESCRIPTION

The present invention relates to monoclonal antibodies reactive with IgE. These monoclonal antibodies are highly useful for preventing the binding of IgE to the mast cell FcE receptor both in vitro and in vivo. These antibodies have the added advantage of not blocking the binding of IgE to the B-cell FcE receptor such that these antibodies will not interfere with associated immune regulatory events.

The general method used for production of hybridomas secreting monoclonal antibodies is well known to those of ordinary skill in the art. Illustrative of the techniques utilized in the present invention are those described in *Proceedings of the National Academy of Science, USA*, 75: 3405, (1978) and Koprowski, U.S. Pat. No. 4,172,124 entitled "Method of Producing Tumor Antibodies."

In brief, BALB/c mice were immunized with IgE myeloma proteins IR2 and IR162 and later boosted with these same proteins. Four days after the last immunization the animals were sacrificed and spleen cells fused with a mouse non-secretor myeloma cell line. Hybridomas were screened for antibody production and positive clones were tested for monoclonal antibody binding to various classes and sub-classes of antibodies.

The isolation of hybridomas secreting monoclonal antibodies with the reactivity of the monoclonal antibodies of the invention can be accomplished using routine screening techniques to determine the elementary reaction pattern of the monoclonal antibody of interest. Thus, if a monoclonal antibody being tested reacts with unbound IgE and with IgE when IgE is bound to the B lymphocyte FcE receptor, but does not react with IgE when the IgE molecule is bound to the mast cell FcE receptor, then the antibody being tested and the antibody produced by the hybridomas of the invention are equivalent.

The isolation of other hybridomas secreting monoclonal antibodies with the specificity of monoclonal antibody 44.7b, or any other monoclonal antibody of the invention, can be accomplished by one of ordinary skill in the art by producing anti-idiotypic antibodies (Herlyn, et al., *Science*, 232: 100, 1986). An anti-idiotypic antibody is an antibody which recognizes unique determinants present on the monoclonal antibody produced by the hybridoma of interest. These determinants are located in the hypervariable region of the antibody. It is this region which binds to a given epitope and, thus, is responsible for the specificity of the antibody. The anti-idiotypic antibody can be prepared by immunizing an animal with the monoclonal antibody of interest. The animal immunized will recognize and respond to the idiotypic determinants of the immunizing antibody by producing an antibody to these idiotypic determinants. By using the anti-idiotypic antibodies produced by the second animal, which are specific for the monoclonal antibodies produced by a single hybridoma which was used to immunize the second animal, it is now possible to identify other clones with the same idiotype as the antibody of the hybridoma used for immunization and thereby greatly simplify and reduce the amount of screening needed to find other hybridomas secreting monoclonal antibodies with the specificity of the monoclonal antibodies of the invention.

Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

Alternatively, it is possible to evaluate, without undue experimentation, a monoclonal antibody to determine whether it has the same specificity as MAb 44.7b of the invention by determining whether the monoclonal antibody being tested prevents the MAb 44.7b from binding to a particular antigen, for example IgE, with which MAb 44.7b is normally reactive. If the monoclonal antibody being tested competes with MAb 44.7b, as shown by a decrease in binding by MAb 44.7b, then it is likely that the two monoclonal antibodies bind to the same epitope.

Still another way to determine whether a monoclonal antibody has the specificity of MAb 44.7b is to pre-incubate MAb 44.7b with an antigen with which it is normally reactive, for example, rat IgE, and determine if the monoclonal antibody being tested is inhibited in its ability to find the antigen. If the monoclonal antibody being tested is inhibited then, in all likelihood, it has the same epitopic specificity as the monoclonal antibody of the invention.

While the in vivo use of monoclonal antibody from a foreign donor species in a different host recipient species is usually uncomplicated, a potential problem which may arise is the appearance of an adverse immunological response by the host to antigenic determinants present on the donor antibody. In some instances, this adverse response can be so severe as to curtail the in vivo use of the donor antibody in the host. Further, the adverse host response may serve to hinder the immediate hypersensitivity ameliorating efficacy of the donor antibody. One way in which it is possible to circumvent the likelihood of an adverse immune response occurring in the host is by using chimeric antibodies (Sun, et al., *Hybridoma*, 5 (Supplement 1): S17, 1986; Oi, et al., *Bio Techniques*, 4 (3): 214, 1986). Chimeric antibodies are antibodies in which the various domains of the antibody heavy and light chains are coded for by DNA from more than one species. Typically, a chimeric antibody will comprise the variable domains of the heavy ($V_H$) and light ($V_L$) chains derived from the donor species producing the antibody of desired antigen specificity and the constant antibody domains of the heavy ($C_H$) and light ($C_L$) chains derived from the host recipient species. It is believed that by reducing the exposure of the host immune system to the antigenic determinants of the donor antibody domains, especially those in the $C_H$ region, the possibility of an adverse immunological response occurring in the recipient species will be reduced. Thus, for example, it is possible to produce a chimeric antibody for in vivo clinical use in a species other than rat which comprises mouse $V_H$ and $V_L$ domains coded for by DNA isolated from ATCC HB 9436 and $C_H$ and $C_L$ domains coded for by DNA isolated from the species of therapeutic interest.

Under certain circumstances, monoclonal antibodies of one isotype might be more preferable than those of another in terms of their diagnostic or therapeutic efficacy. For example, from studies on antibody-mediated cytolysis it is known that unmodified mouse monoclonal antibodies of isotype gamma-2a and gamma-3 are generally more effective in lysing target cells than are antibodies of the gamma-1 isotype. This differential efficacy is thought to be due to the ability of the gamma-2a and gamma-3 isotypes to more actively participate in the cytolytic destruction of the target cells. Particular isotypes of a monoclonal antibody can be prepared either directly, by selecting from the initial fusion, or prepared secondarily, from a parental hybridoma secreting monoclonal antibody of different isotype, by using the sib selection technique to isolate class-switch variants (Steplewski, et al., *Proceedings of National Academy of Science, USA*, 82: 8653, 1985; Spira, et al., *Journal of Immunological Methods*, 74: 307, 1984). Thus, the monoclonal antibodies of the invention would include class-switch variants having the specificity of monoclonal antibody 44.7b which is produce by ATCC HB 9436.

The monoclonal antibodies of the invention can be used in any animal in which it is desirable to administer in vivo immunotherapy to block the immediate hypersensitivity response. The term "animal" as used herein is meant to denote non-humans.

The term "antibody" as used in this invention is meant to include intact molecules as well as fragments thereof, such as, for example, Fab and F(ab')$_2$, which are capable of binding the epitopic determinant.

As used in this invention, the term "epitope" is meant to include any determinant capable of specific interaction with the monoclonal antibodies of the invention. Epitopic determinants usually consist of chemically active surface groupings of molecules such as amino acids or sugar side chains and usually have specific three dimensional structural characteristics, as well as specific charge characteristics.

The term "ameliorate" denotes a lessening of the detrimental affect of the immediate hypersensitivity response in the animal receiving therapy. The term "therapeutically effective" means that amount of the monoclonal antibody of the invention which is capable of ameliorating the immediate hypersensitivity response.

The dosage ranges for the administration of the monoclonal antibodies of the invention are those large enough to produce the desired effect in which the symptoms of immediate hypersensitivity are ameliorated. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications, immune tolerance or similar conditions. Dosage can vary from about 0.1 mg/m$^2$ to about 2000 mg/m$^2$, preferably from about 0.1 mg/m$^2$ to about 500 mg/m$^2$/dose, in one or more dose administrations daily, for one or several days.

The antibodies can be administered parenterally by injection or by gradual perfusion over time. The monoclonal antibodies of the invention can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as, olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, and inert gases and the like.

The invention also relates to a method for preparing a medicament or pharmaceutical composition comprising the monoclonal antibodies of the invention, the medicament being used for therapy of tumors expressing antigens reactive with the monoclonal antibodies of the invention.

Since the monoclonal antibodies of the invention bind an epitope which is in the IgE Fc domain which, in turn, interacts with the mast cell FcE receptor, it is possible to use the antibodies of the invention to map the FcE receptor interaction sites. By determining the amino acid sequence of the peptide epitope for which the monoclonal antibodies of the invention are specific, it is reasonable that these peptides could be used to, in effect, saturate an animal's mast cell receptor sites and, thereby, prevent IgE from binding to the, mast cell FcE receptor. The identification of the epitope specifically bound by the monoclonal antibodies of the invention can be determined by using well-known proteolytic enzymes in order to determine the exact peptide fragment having the epitope (Stanworth, et al., *Molecular Immunology*, 23(11), 1231, 1986). Once the Fc peptide fragment containing the epitope has been isolated, the amino acid sequence can be readily determined using known techniques. It would then be a matter of routine to prepare large quantities of the peptide comprising the epitope, for example, by using amino acid synthesizers or by recombinant DNA techniques, such as by transforming an organism with a cDNA molecule coding for mRNA which, when translated, results in high levels of peptide.

Monoclonal antibody 44.7b is obtained from, or has the identifying characteristics of, an antibody obtained from the cell line having ATCC accession number HB 9436. This cell line was placed on deposit for 30 years at the American Type Culture Collection (ATCC) in Rockville, Md. prior to Jun. 8, 1987.

The above disclosure generally describes the present invention. A more complete understanding can be obtained by reference to the following specific examples which are provided herein for purposes of illustration only, and are not intended to limit the scope of the invention.

EXAMPLE 1

General Analytical Techniques

A. Rat Immunoglobulins and Cell Lines

IR2 and IR162, two rat IgE myeloma proteins originally described by Bazin et al. (*Immunology*, 26: 713, 1974), were used for immunization. IR2, biotinylated IgE, purified rat serum IgG, and rat myeloma proteins of other isotypes were obtained from Zymed (San Francisco, Ca.). IR162 was kindly provided by Dr. A. Kulcyzski (Washington University, St. Louis, Mo.).

The RBL-1 cell line was obtained from the American Type Culture Collection (ATCC 72307 Parklawn Drive, Rockville, Md. 20852). The RBL-2H3 cell line was kindly provided by Dr. Henry Metzger (NIH, Bethesda, Md.). The A3 cell line was kindly provided by Dr. Daniel Conrad (John Hopkins, Baltimore, Md.). The A3 cell line was incubated with BSF-1-containing EL-4 supernatant for 24 hrs before use to increase FcE receptor expression. The HAT-sensitive cell line SP2/0 was obtained from the Hybridoma Center, Washington University Medical Center, St. Louis, Mo.) and from the ATCC (Rockville, Md.). These cells were maintained in DMEM plus 15% Hyclone FBS, glutamine, nonessential amino acids and gentamycin.

B. IgE-specific Antibodies

B5 and A2, are hybridomas secreting IgE specific monoclonal antibodies (Conrad, et al., *International Archives of Allergy and Applied Immunology*, 70: 352, 1983) were donated by Dr. Daniel Conrad (Johns Hopkins, Baltimore, Md.). A second anti-IgE monoclonal antibody, MARE-1, was obtained from Serotec (Bioproducts for Science, Inc., Indianapolis, Ind.). The 44.7*b* and MARE-1 monoclonal antibodies (at 1 mg/ml in 0.1M NaHCO$_3$, pH 8.6) were incubated at room temperature with biotinyl-succinyl ester for 3 hr and excess biotin was removed by dialysis in Tris buffer (50 mM Tris, 150 mM NaCl, pH 7.4).

Inhibition Assay for IgE Binding to RBL Cells

Biotin-IgE (1 ug/test sample) was incubated alone or with monoclonal anti-IgE antibodies for 1 hr at 37° C. RBL cells ($5 \times 10^5$ cells in 50 ul) were added to 50 ul of the pre-incubated biotin-IgE plus antibody preparations and incubated for 20 min on ice. The cells were washed 3× followed by addition of FITC-avidin (Vector, Burlingame, Calif., 1 ug/sample) and incubated for 20 min at 37° C. Cells were washed 3× before flow cytometry analysis.

Assay for Monoclonal Antibody Binding to Cell-Bound IgE

RBL or A3 cells ($5 \times 10^5$ cells in 50 ul) were incubated with mouse IgG1 for 30 min on ice to block FcG receptors. IgE (1 ug/test sample for RBL cells or 5 ug/sample for A3 cells) was added for 20 min and the cells were washed 3× before addition of biotin-44.7*b* or biotin-MARE. After a 20 min incubation cells were further treated with FITC-avidin as described above.

E. Flow Cytometry

Cells were analyzed using an Epics 753 flow cytometer (Coulter, Hialeah, Fla.). Cells were gated to exclude non-viable cells based on forward angle light scatter (cell size) and log 90° light scatter (cell complexity). Log green fluorescence histograms were collected on 10,000 gated cells. All graphics were produced on the RCC-Vax system using software written utilizing the Tellagraf graphics command language (ISSCO, San Diego, Calif.).

EXAMPLE 2

Preparation of Hybridoma Cell Lines Producing Monoclonal Antibodies to Rat IgE

Balb/c mice (Jackson Labs, Portland, Me.) were initially injected i.p. with 100 ug of IR2 (Zymed Labs, San Francisco, Calif.) in 0.1 ml of complete Freund's Adjuvent (Difco, Detroit, Mich.). Three weeks later the animals were boosted with 100 ug of IR2 i.p. followed in two weeks by a final i.p. injection of 100 ug of IR162. Four days after the last immunization, spleen cells were removed and a single cell suspension was prepared. Red cells were lysed in 0.85% NH$_4$Cl. Spleen cells at approximately $8 \times 10^7$/tube were mixed with $4 \times 10^7$ SP2/0 cells, centrifuged, and the media was completely removed. One ml of PEG 1450 (Sigma, St. Louis, 40% in DMEM) +5% DMSO was added dropwise over 1 min with regular agitation of the tube. One ml of DMEM was added slowly over the next min. During the next 2.5 min the cells were slowly diluted with an additional 9 ml of DMEM. The cells were centrifuged (1000 rpm, 8 min) and resuspended in DMEM+15% hyclone FBS before being placed at approximately $1-2 \times 10^5$ cells/well (based original counts) in 96-well plates. The cells were fed on days 1 and 2 following fusion with a total of 200 ul/well of DMEM 15% FBS plus HAT. Under these conditions, 95–100% of the wells are positive for growth of hybrids within 2 weeks.

EXAMPLE 3

Characterization of Monoclonal Antibody 44.7*b*

A. Specificity

Figure 1:
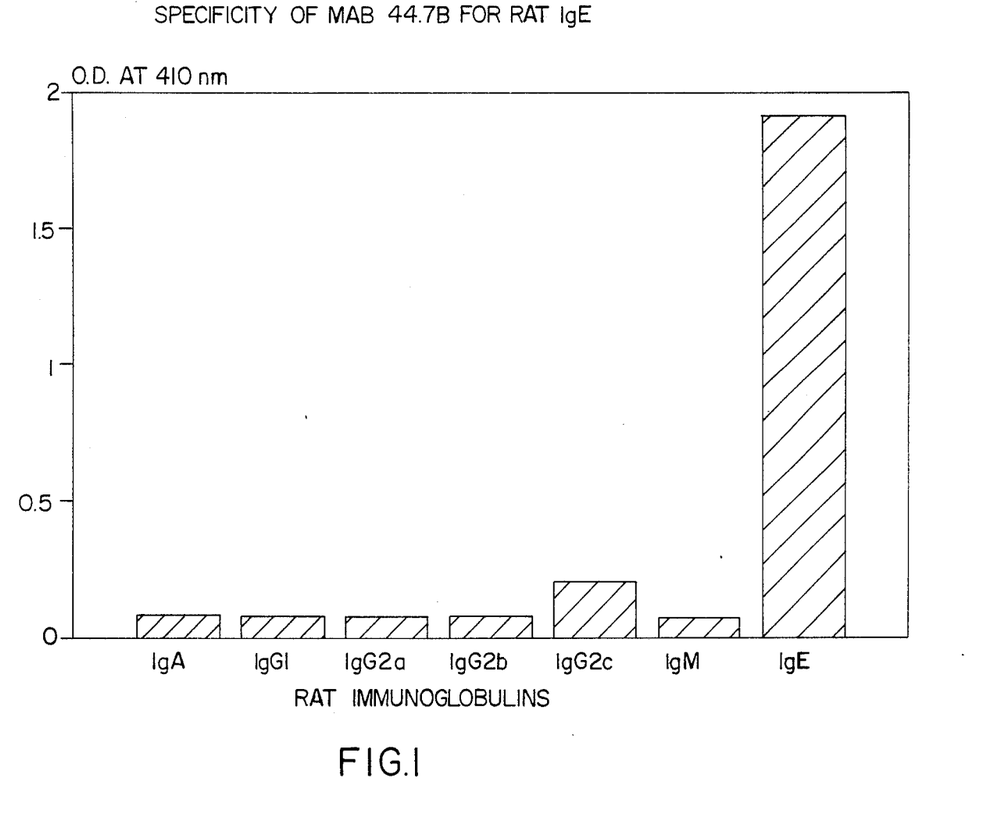
FIG. 1 is a chart showing MAb 44.7b reactivity against rat myeloma proteins.

The hybridoma producing the 44.7*b* antibody was isolated from a fusion of spleen cells from Balb/c mice immunized with rat IgE (IR2 and IR162 myeloma proteins) and the HAT-sensitive cell line SP2/0. Subclones of this line were shown to produce an IgG1, kappa antibody. To further characterize the antibody, 44.7*b* was tested in an ELISA assay using plates coated with myeloma proteins of the IgE, IgG1, IgG2*a*, IgG2*b*, IgM and IgA isotypes. As shown in FIG. 1, the 44.7*b* antibody reacted with rat IgE but not other rat immunoglobulin isotypes. The 44.7*b* antibody reacts with both IR2 and IR162 myeloma proteins indicating that it is not idiotype-specific.

B. Inhibition of IgE Binding To Rat Mast Cells

Figure 2:
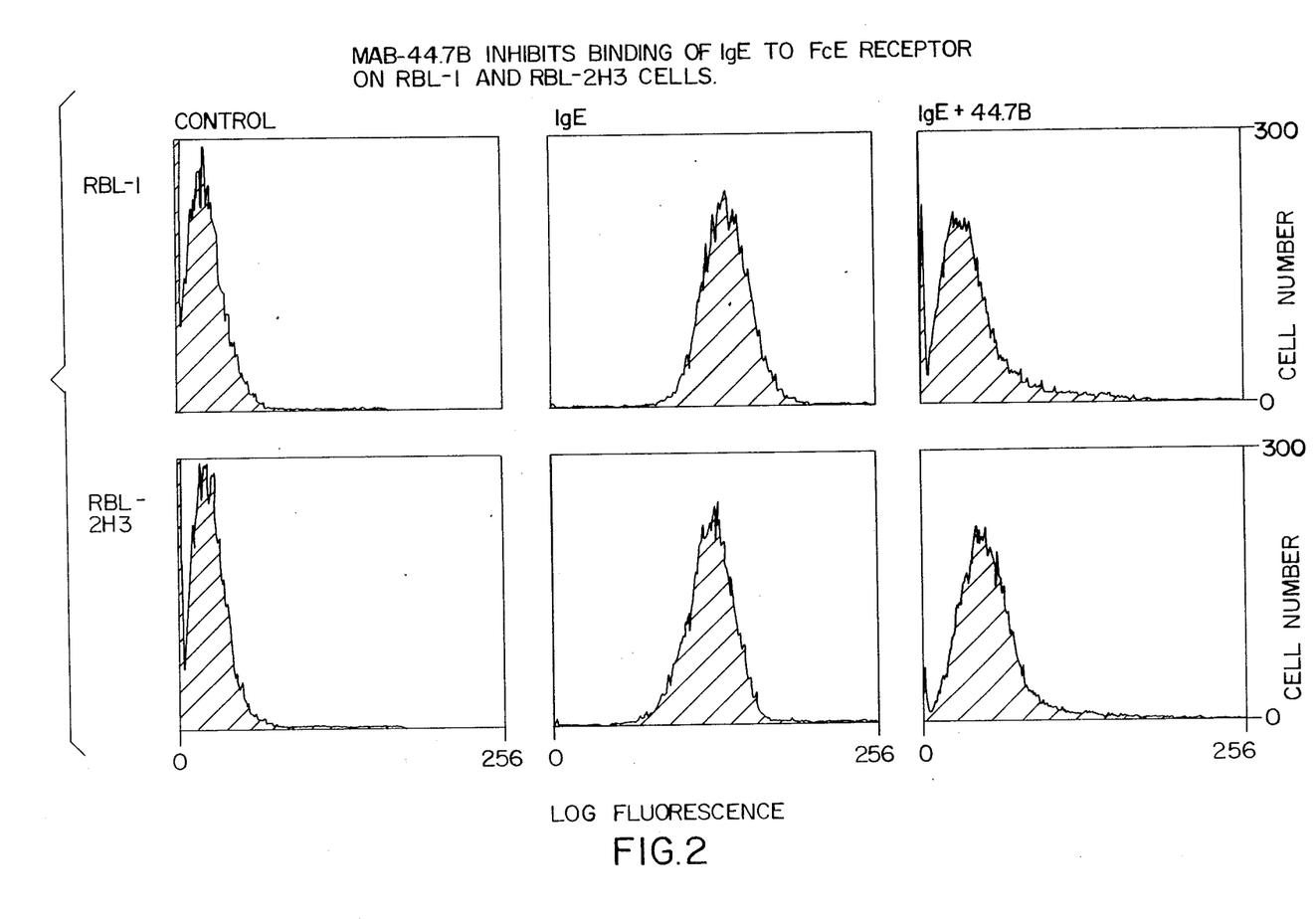
FIG. 2 depicts flow cytometry readings showing the ability of MAb 44.7b to inhibit binding of IgE to the high-affinity FcE receptors on the rat mast cell-like lines, RBL-1 and RBL-2H3.

The cell lines RBL-1 and a variant, RBL-2H3, appear to be closely related to mucosal mast cells (Seldin, et al., *Proceedings of the National Academy of Sciences*, 82: 3871, 1985) and express large numbers of high affinity FcE receptors. To determine whether the 44.7*b* monoclonal antibody could inhibit IgE binding to these cells, biotin-IgE was preincubated with 44.7*b* or media for 1 hr. at 37° C. before addition to RBL cells. Avidin-FITC was added to detect RBL cell-bound IgE and the results were analyzed by flow cytometry. As shown in FIG. 2, the 44.7*b* monoclonal antibody inhibited IgE binding to RBL cells suggesting that the epitope recognized by this antibody is within or close to the site bound by the high affinity FcE receptor.

C. Specificity of 44.7b Inhibition of IgE-Mast Cell Binding

Figure 3:
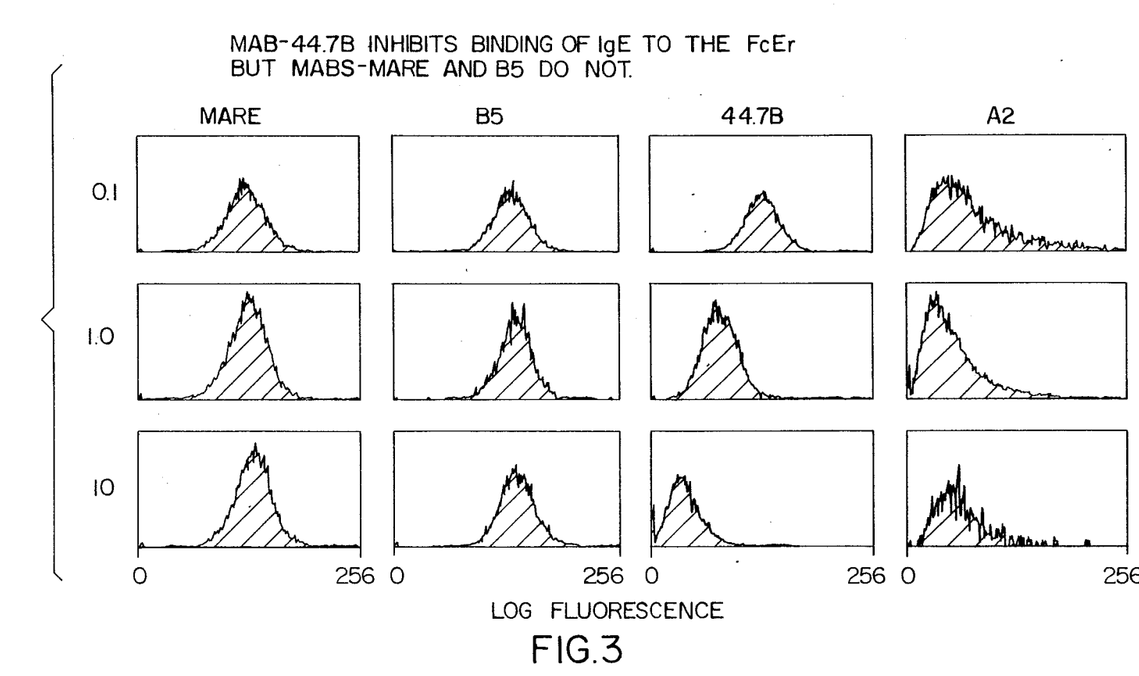
FIG. 3 depicts flow cytometry readings comparing four different IgE-specific MAbs.

The IgE-specific 44.7b monoclonal antibody inhibits IgE binding to RBL cells. Several other monoclonal antibodies to rat IgE have been described (Conrad, et al., *International Archives of Allergy and Applied Immunology*, 70: 352, 1983; Manowriez, et al., *Annals of the Institute Pasteur Immunologie*, 136: C187, 1985). These antibodies were also tested for ability to inhibit IgE binding to RBL FcE receptors. The results in FIG. 3 confirm that 44.7b inhibits IgE binding to mast cells in a dose dependent fashion. In contrast, these other IgE-specific monoclonal antibodies (MARE-1,A2 and B5) did not block IgE-mast cell interaction. Therefore, the IgE epitope recognized by 44.7b can be distinguished from the epitope(s) recognized by these other antibodies.

D. 44.7b Non-Reactivity with RBL cell bound IgE

Figure 4:
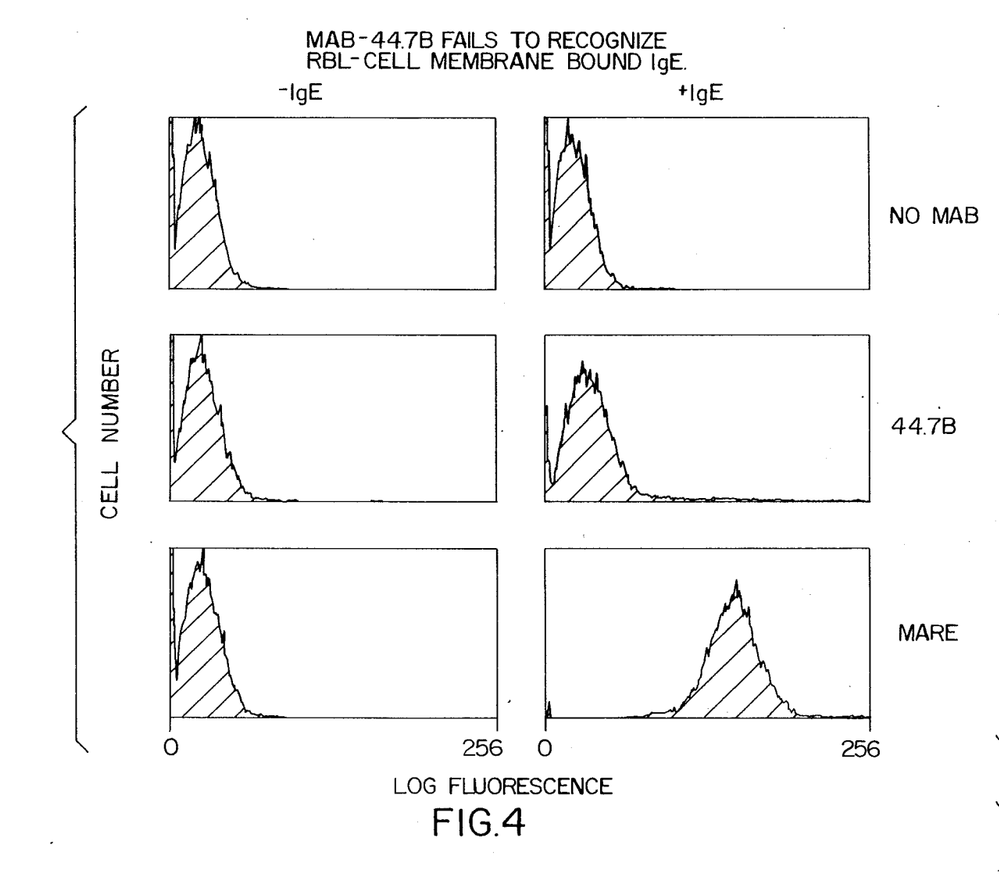
FIG. 4 depicts flow cytometry readings demonstrating that a monoclonal antibody of the invention will not bind to IgE already bound to a mast cell FcE receptor.

The results presented above suggest that IgE epitope recognized by 44.7b is within or close to the IgE Fc domain recognized by the mast cell FcE receptor. Other antibodies to IgE have been described which partially inhibit IgE binding to mast cells but also react with IgE already bound to the mast cell FcE receptor (Baniyash, et al., European Journal of Immunology, 14: 799, 1984). To determine if the 44.7b monoclonal antibody acts in a similar manner, rat IgE was attached to RBL cells. Biotin-labeled 44.7b or MARE-1 were added to these cells followed by FITC-avidin. Since RBL cells have FcG receptors, the cells were precubated with mouse IgG1. IgG1 was also added to the incubation buffers to block any Fc-mediated binding of the biotinylated monoclonal antibodies (both IgG1 antibodies). As shown in FIG. 4, the MARE-1 antibody bound to IgE on the surface of RBL cells. In contrast, little staining of the RBL cell-bound IgE by 44.7b was observed, indicating that the epitope recognized by 44.7b is not exposed on IgE bound to the RBL cell FcE receptor. These results further support the data presented supra that 44.7b recognizes a site on the IgE molecule which is within or close to the IgE Fc domain to which the mast cell FcE receptor binds.

E. 44.7b Recognition of IgE Bound to the B-cell FcE Receptor

Figure 5:
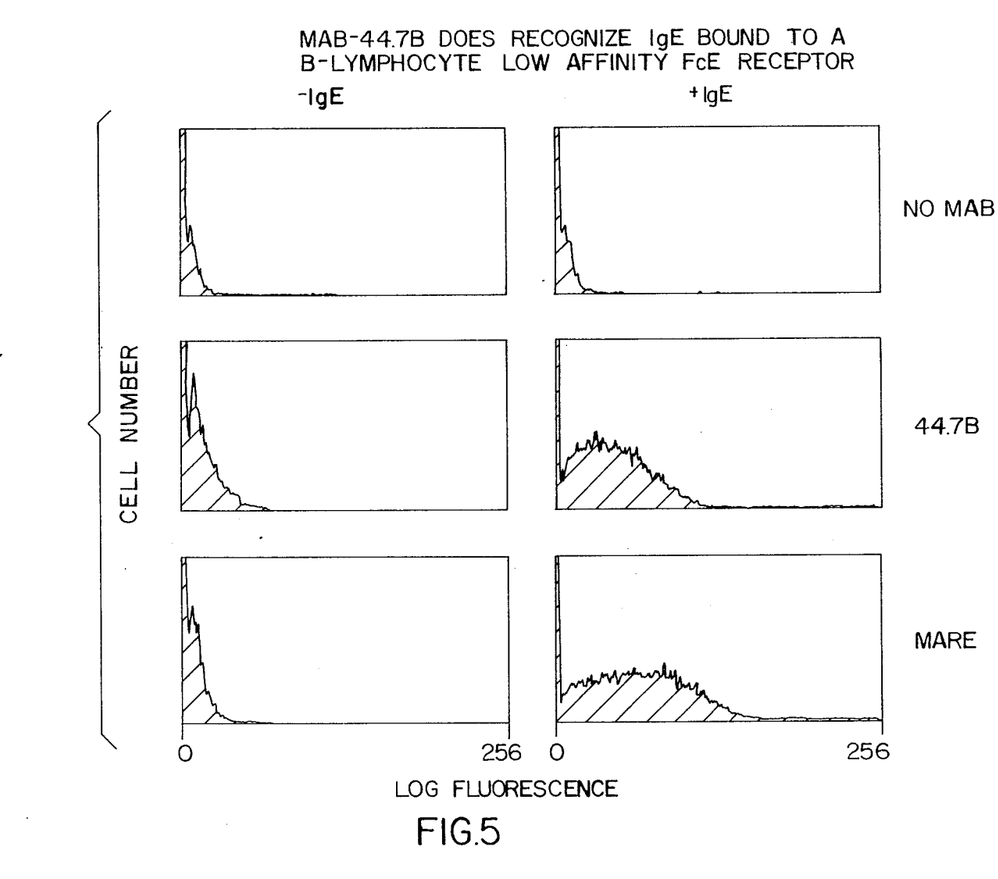
FIG. 5 depicts flow cytometry readings demonstrating the ability of a monoclonal antibody of the invention to bind IgE already bound to a B lymphocyte FcE receptor.

The high affinity FcE receptors on mast cells and the low affinity receptors on other cells differ in structure and amino acid sequence. Thus, the manner in which these receptors bind IgE may be different. To determine whether the IgE epitopes recognized by mast cells and B lymphocyte FcE receptors are distinct, the ability of the 44.7b monoclonal antibody to recognize IgE bound to the surface of the murine B lymphocyte cell line, A3, was examined. Although the A3 cell line is of murine origin, it binds rat and mouse IgE with similar affinities. A3 cells were cultured overnight with IL4 (BSF-1)- containing supernatant from EL-4 cells. The A3 cells also were preincubated with mouse IgG1 to inhibit FcG receptor-mediated binding of the monoclonal anti-IgE antibodies. The cells were then stained with biotin-44.7b or biotin-MARE-1 and analyzed by flow cytometry as described supra. As shown in FIG. 5, the staining of these cells was always weaker than RBL cells due to the lower affinity of the lymphocyte receptors for IgE. However, the amount of fluorescence observed on cells stained with the MARE-1 and 44.7b monoclonal antibodies was similar indicating that IgE epitopes recognized by these antibodies are exposed when IgE is bound to B lymphocytes.

Thus, the epitope recognized by the 44.7b monoclonal antibody is accessible when IgE is bound to the FcE receptor of a B lymphocyte even though the epitope is not exposed when the IgE is bound to the FcE receptor of the mast cell. These results suggest that FcE receptors on mast cells and on B cells bind to different regions of the IgE molecule.

EXAMPLE 4

Non-Reactivity of 44.7b with Human IgE and Mouse IgE

Microtiter plates were coated with 1 ug/ml of either rat IgE (IR2 myeloma protein), human IgE (Chemicon, El Segundo, Calif.), or mouse IgE (ICN Immunobiologicals, Lisle, Ill.). Dilutions of biotinylated 44.7b were added to the plates and incubated for 90 min at 37° C. Avidin-horseradish peroxidase (1 ug/well, Vector Labs, Burlingam, Calif.) was added for an additional 90 min at 37° C. followed by addition of enzyme substrate (OPD) in substrate buffer (Zymed, San Francisco, Calif.) for 30 min at room temperature. The optical density was read at 492 mm using a Dynatec Elisa Reader (Dynatec Labs, Alexandria, Va.). MAb 44.7b was found to react strongly with rat IgE, but showed no reaction with either mouse IgE or human IgE.

The invention now being fully described, it will be apparent to one of ordinary skill in the art that many changes and modifications can be made without departing from the spirit or scope of the invention.

We claim:

1. The monoclonal antibody produced by hybridoma cell line ATCC HB 9436 which specifically binds to IgE and inhibits binding of the IgE to a mast cell FcE receptor and which does not bind to IgE when IgE is bound to a mast cell FcE receptor, but does bind to IgE when IgE is bound to a B-cell FcE receptor.

2. The hybridoma which is deposited at the American Type Culture Collection under accession number ATCC HB 9436.

* * * * *

UNITED STATES PATENT AND TRADEMARK OFFICE
CERTIFICATE OF CORRECTION

PATENT NO. : 4,940,782
DATED : July 10, 1990
INVENTOR(S) : Rup et al.

It is certified that error appears in the above-identified patent and that said Letters Patent is hereby corrected as shown below:

Column 1, line 50, reading "1975" should read -- 1975 --.

Column 4, line 22, reading "for example" should read -- for example rat --.

Column 5, line 24, reading "produce" should read -- produced --.

Column 7, line 7, reading "72307" should read -- 12301 --.

Column 7, line 36, reading "Inhibition Assay for..." should read -- C. Inhibition Assay for... --.

Column 7, line 48, reading "Assay for Monoclonal..." should read -- D. Assay for Monoclonal... --.

Signed and Sealed this

Twenty-fourth Day of August, 1993

Attest:

BRUCE LEHMAN

*Attesting Officer*     *Commissioner of Patents and Trademarks*